US012629138B2

(12) United States Patent
Haney et al.

(10) Patent No.: US 12,629,138 B2
(45) Date of Patent: May 19, 2026

(54) SYSTEMS AND METHODS FOR GENERATING MENSTRUAL CYCLE COHORTS AND CLASSIFYING USERS INTO A COHORT

(71) Applicant: Google LLC, Mountain View, CA (US)

(72) Inventors: S Ariel Haney, Oakland, CA (US); Belen Lafon, San Francisco, CA (US); Jacqueline Deanne Baras Shreibati, Menlo Park, CA (US)

(73) Assignee: GOOGLE LLC, Mountain View, CA (US)

( * ) Notice: Subject to any disclaimer, the term of this patent is extended or adjusted under 35 U.S.C. 154(b) by 705 days.

(21) Appl. No.: 18/083,989

(22) Filed: Dec. 19, 2022

(65) Prior Publication Data

US 2023/0210503 A1 Jul. 6, 2023

Related U.S. Application Data

(60) Provisional application No. 63/295,179, filed on Dec. 30, 2021.

(51) Int. Cl.
*A61B 10/00* (2006.01)
*A61B 5/00* (2006.01)
(Continued)

(52) U.S. Cl.
CPC .......... *A61B 10/0012* (2013.01); *A61B 5/024* (2013.01); *A61B 5/4806* (2013.01);
(Continued)

(58) Field of Classification Search
CPC ... A61B 10/0012; A61B 5/024; A61B 5/4806; A61B 5/6802; A61B 5/7246;
(Continued)

(56) References Cited

U.S. PATENT DOCUMENTS

2020/0000441 A1\* 1/2020 Lafon ................ A61B 5/02438
2020/0321077 A1 10/2020 Taylor et al.
2024/0016456 A1\* 1/2024 de Zambotti ...... A61B 5/02055

FOREIGN PATENT DOCUMENTS

KR 20200063507 A \* 6/2020 ......... A61B 5/02108

OTHER PUBLICATIONS

Inside Big Data, "Meet Flo—The First Period & Ovulation Tracker that Uses Neural Networks.", May 21, 2017, https://insidebigdata.com/2017/05/21/meet-flo-first-period-ovulation-tracker-uses-neural-networks/, retrieved on Jan. 27, 2023, 3 pages.

\* cited by examiner

*Primary Examiner* — Devin B Henson
*Assistant Examiner* — Molly Halprin
(74) *Attorney, Agent, or Firm* — DORITY & MANNING P.A.

(57) ABSTRACT

Provided are systems for grouping users who have chosen to participate into one of a plurality of menstrual cycle groups based on data provided by and/or collected from those users. In some examples, a wearable computing device can include one or more sensors that can measure one or more physiological signals associated with the user. Based on the physiological signals gathered from the one or more sensors, the wearable computing device can determine biometric data for one or more users. Furthermore, the wearable computing device can enable a user to submit information about their menstrual cycle (e.g., via an interactive touch screen). These factors can be used to automatically determine some menstrual cycle data for a user.

20 Claims, 8 Drawing Sheets

(51) Int. Cl.
   *A61B 5/024*          (2006.01)
   *G16H 50/70*          (2018.01)

(52) U.S. Cl.
   CPC .......... *A61B 5/6802* (2013.01); *A61B 5/7246*
              (2013.01); *A61B 5/7264* (2013.01); *A61B
      *5/742* (2013.01); *G16H 50/70* (2018.01); *A61B
                              *2010/0029* (2013.01)

(58) Field of Classification Search
   CPC .................. A61B 5/7264; A61B 5/742; A61B
                2010/0029; A61B 5/743; A61B 5/318;
              A61B 5/389; A61B 5/398; A61B 5/681;
                  A61B 5/6824; A61B 5/6826; A61B
          5/0022; A61B 5/01; A61B 5/02055; A61B
              5/02405; A61B 5/1118; A61B 5/4306;
              A61B 5/7267; A61B 2010/0019; G16H
                  50/70; G16H 40/67; G16H 50/20
   USPC ....................................................... 600/551
   See application file for complete search history.

100

102

104

106

○ BEACH
□ MEDITERRANEAN
◇ TEMP. FOREST HR
△ CORAL REEF
☆ TEMP.FOREST SLEEP
○ RAINFOREST HR
○ RAINFOREST +SLEEP
○ RAINFOREST -SLEEP

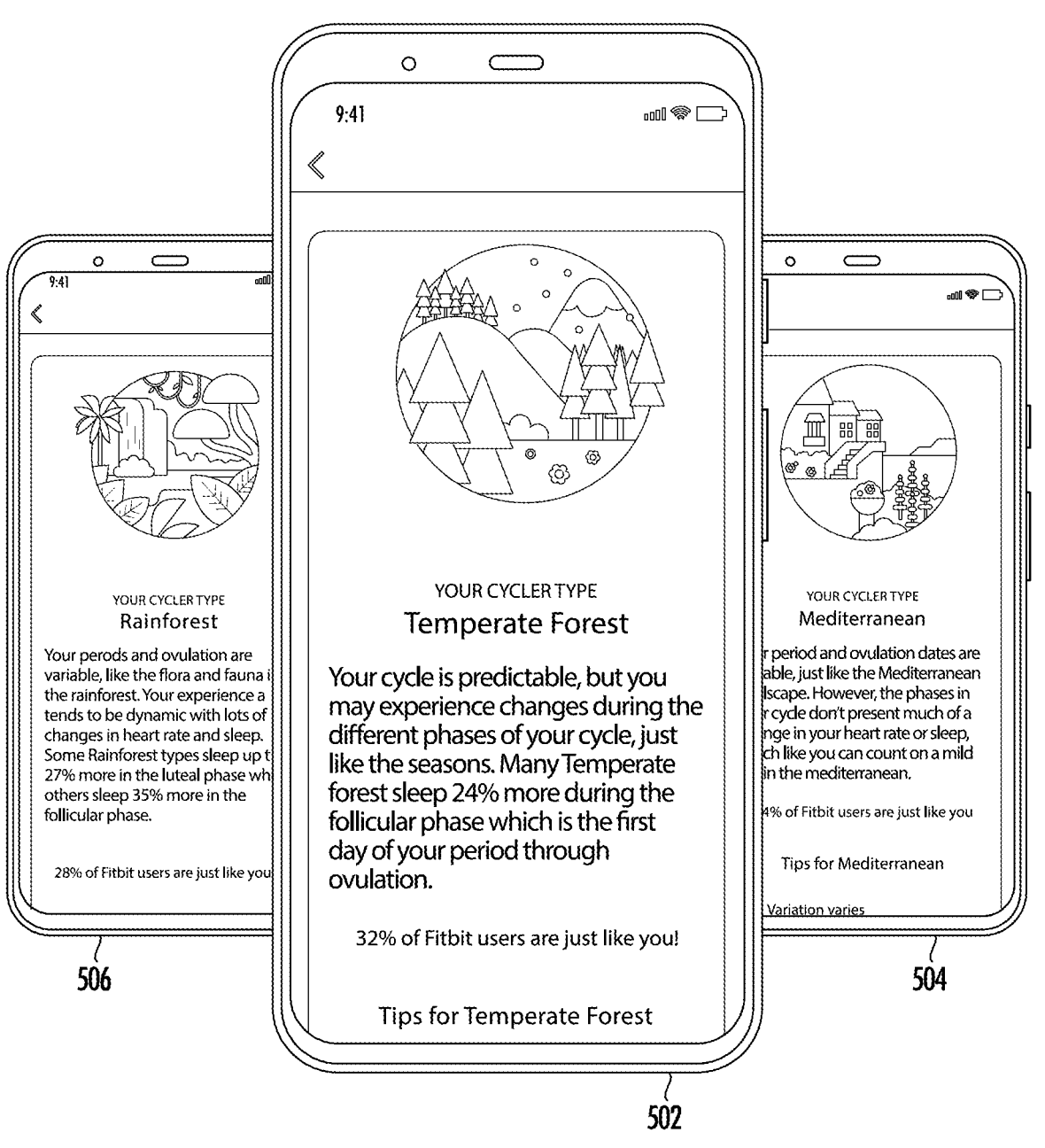

9:41

YOUR CYCLER TYPE
Rainforest

Your perods and ovulation are variable, like the flora and fauna i the rainforest. Your experience a tends to be dynamic with lots of changes in heart rate and sleep. Some Rainforest types sleep up t 27% more in the luteal phase wh others sleep 35% more in the follicular phase.

28% of Fitbit users are just like you

506

9:41

YOUR CYCLER TYPE
Temperate Forest

Your cycle is predictable, but you may experience changes during the different phases of your cycle, just like the seasons. Many Temperate forest sleep 24% more during the follicular phase which is the first day of your period through ovulation.

32% of Fitbit users are just like you!

Tips for Temperate Forest

502

YOUR CYCLER TYPE
Mediterranean r period and ovulation dates are able, just like the Mediterranean lscape. However, the phases in r cycle don't present much of a nge in your heart rate or sleep, ch like you can count on a mild in the mediterranean.

4% of Fitbit users are just like you

Tips for Mediterranean

Variation varies

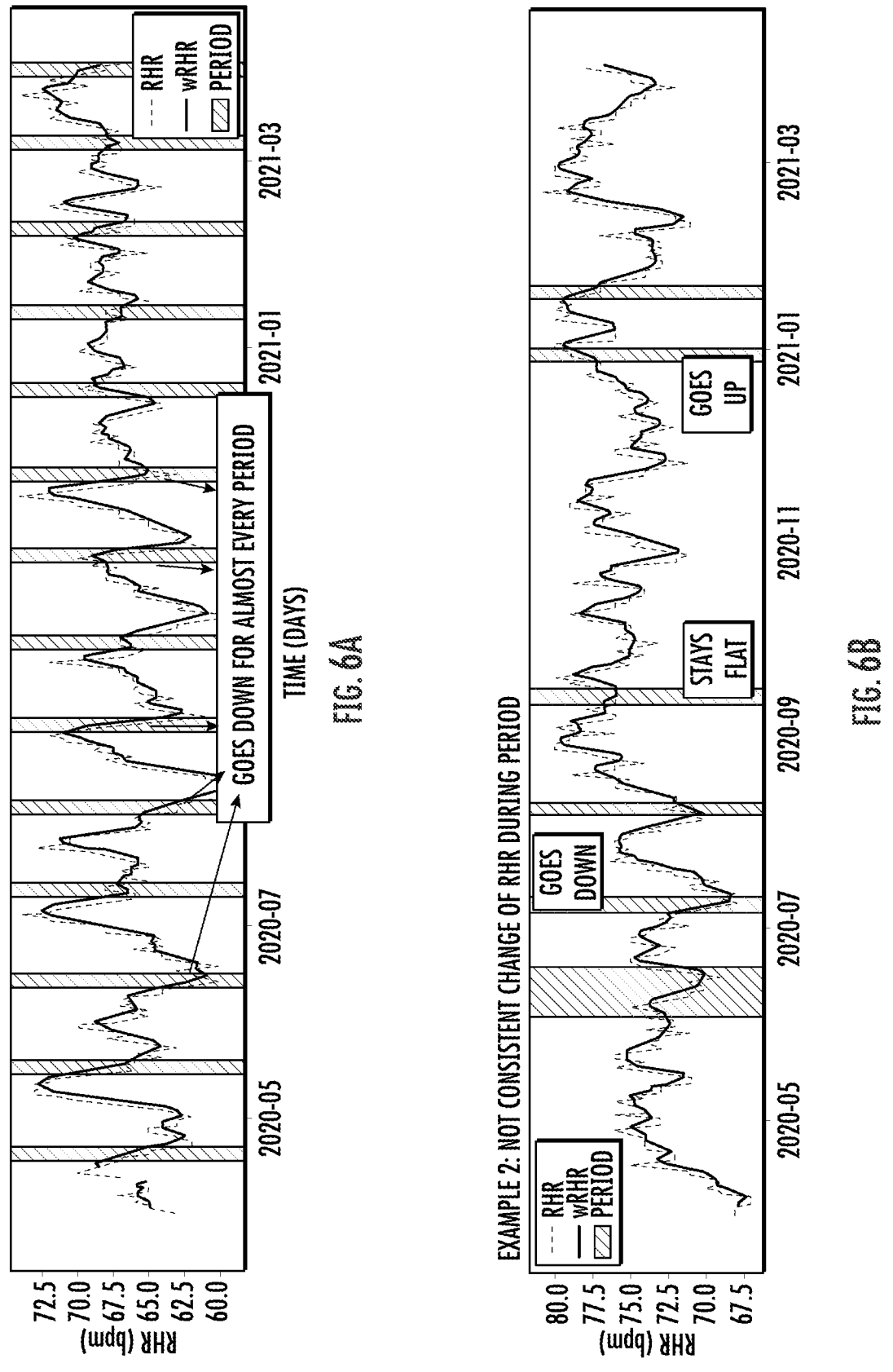

INPUT DATA

706

CYCLE GROUP CLASSIFICATION SYSTEM
700

OUTPUT DATA

708

HISTORICAL
USER DATA

716

CLUSTER GENERATION SYSTEM
310

CLUSTER
GROUP
DEFINITION
DATA

718

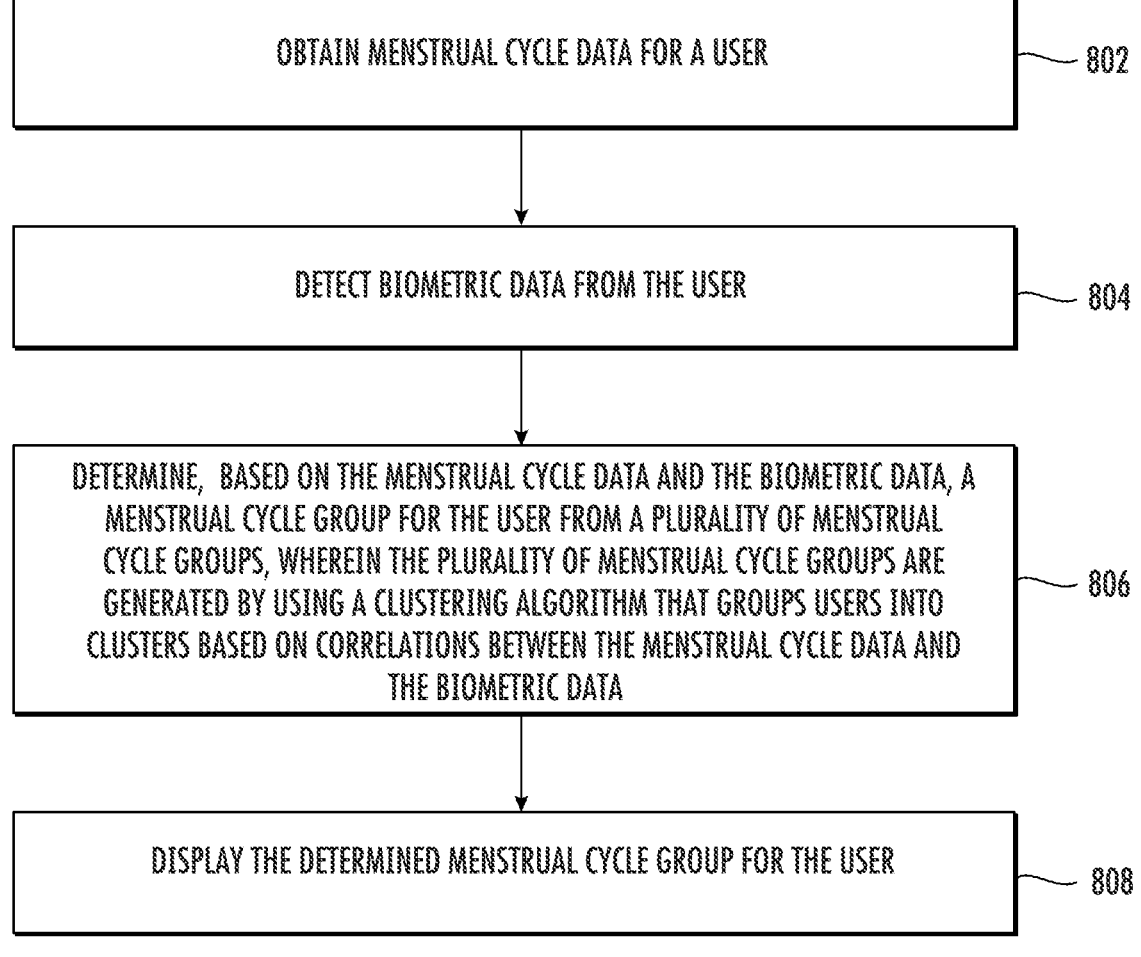

OBTAIN MENSTRUAL CYCLE DATA FOR A USER — 802

DETECT BIOMETRIC DATA FROM THE USER — 804

DETERMINE, BASED ON THE MENSTRUAL CYCLE DATA AND THE BIOMETRIC DATA, A MENSTRUAL CYCLE GROUP FOR THE USER FROM A PLURALITY OF MENSTRUAL CYCLE GROUPS, WHEREIN THE PLURALITY OF MENSTRUAL CYCLE GROUPS ARE GENERATED BY USING A CLUSTERING ALGORITHM THAT GROUPS USERS INTO CLUSTERS BASED ON CORRELATIONS BETWEEN THE MENSTRUAL CYCLE DATA AND THE BIOMETRIC DATA — 806

DISPLAY THE DETERMINED MENSTRUAL CYCLE GROUP FOR THE USER — 808

FIG. 8

SYSTEMS AND METHODS FOR GENERATING MENSTRUAL CYCLE COHORTS AND CLASSIFYING USERS INTO A COHORT

PRIORITY CLAIM

The present application is claims priority to U.S. Provisional Application No. 63/295,179, filed on Dec. 30, 2021. The entire contents of that provisional application are hereby incorporated by reference in this patent application.

FIELD

The present disclosure relates generally to analyzing user data to group users into useful groups based on data gathered, at least in part, from wearable computing systems. More particularly, the present disclosure is directed to systems and methods for generating menstrual cycle cohorts and classifying users into a cohort.

BACKGROUND

Recent advances in wearable technology such as fitness trackers and smart watches have enabled, with the consent of the user, the collection of data from sensors included in the wearable computing devices. Such data can be analyzed to provide insights to the user regarding their health, such as metrics regarding sleep, fitness routines, or other health characteristics. However, the data collected for various users can vary such that the systems and tools that accurately evaluate health characteristics for some types of users may be inaccurate when used to analyze the health characteristics for another type of user.

SUMMARY

Aspects and advantages of embodiments of the present disclosure will be set forth in part in the following description, or may be learned from the description, or may be learned through practice of the embodiments.

One example aspect of the present disclosure is directed to a computer-implemented method for association of a user with a menstrual cycle cohort. The method comprises obtaining, by a computing device, menstrual cycle data for the user. The method further comprises detecting, by one or more sensors included in the computing device, biometric data from the user. The method further comprises determining, by the computing device and based on the menstrual cycle data and the biometric data, a menstrual cycle group for the user from a plurality of menstrual cycle groups, wherein the plurality of menstrual cycle groups are generated by performance of a clustering algorithm that groups users into clusters based on correlations between the menstrual cycle data and the biometric data. The method further comprises displaying, in a display associated with the computing device, data representing the determined menstrual cycle group for the user.

Another example aspect of the present disclosure is directed to a system for determining a user's menstrual cycle group. The system comprises a computing system comprising one or more processors, one or more sensors, and a non-transitory computer-readable memory. The non-transitory computer-readable memory stores instructions that, when executed by the processor, cause the computing system to perform operations. The operations comprise obtaining, by the computing system, menstrual cycle data for the user. The operations further comprise detecting, by the one or more sensors included in the computing system, biometric data from the user. The operations further comprise determining, by the computing system and based on the menstrual cycle data and the biometric data, a menstrual cycle group for the user from a plurality of menstrual cycle groups, wherein the plurality of menstrual cycle groups are generated by performance of a clustering algorithm that groups users into clusters based on correlations between the menstrual cycle data and the biometric data. The operations further comprise providing for display, in a display associated with the computing system, data representing the determined menstrual cycle group for the user.

Another example aspect of the present disclosure is directed to a non-transitory computer-readable medium storing instructions that, when executed by one or more computing devices, cause the one or more computing devices to perform operations. The operations comprise obtaining, by the one or more computing devices, menstrual cycle data for a user. The operations further comprise obtaining, by the one or more computing devices, biometric data collected from the user using one or more sensors. The operations further comprise determining, by the one or more computing devices and based on the menstrual cycle data and the biometric data, a menstrual cycle group for the user from a plurality of menstrual cycle groups, wherein the plurality of menstrual cycle groups are generated by using a clustering algorithm that groups users into clusters based on correlations between the menstrual cycle data and the biometric data. The operations further comprise providing, by the one or more computing devices, data representing the determined menstrual cycle group for the user for display to the user.

Other example aspects of the present disclosure are directed to systems, apparatus, computer program products (such as tangible, non-transitory computer-readable media but also such as software which is downloadable over a communications network without necessarily being stored in non-transitory form), user interfaces, memory devices, and electronic devices for implementing and utilizing user computing devices.

These and other features, aspects and advantages of various embodiments will become better understood with reference to the following description and appended claims. The accompanying drawings, which are incorporated in and constitute a part of this specification, illustrate embodiments of the present disclosure and, together with the description, serve to explain the related principles.

BRIEF DESCRIPTION OF THE DRAWINGS

Detailed discussion of embodiments directed to one of ordinary skill in the art are set forth in the specification, which refers to the appended figures, in which:

FIG. 5 illustrates an example user interface display associated with one or more cycler types in accordance with example embodiments of the present disclosure.

FIG. 6A illustrates a representation of data associated with a resting heart rate for a user and cycle information in accordance with example embodiments of the present disclosure.

FIG. 6B illustrates a representation of data associated with a resting heart rate for a user and cycle information in accordance with example embodiments of the present disclosure.

FIG. 8 is a flowchart depicting an example process of determining a cycle group of a user in accordance with example embodiments of the present disclosure.

DETAILED DESCRIPTION

Figure 1:
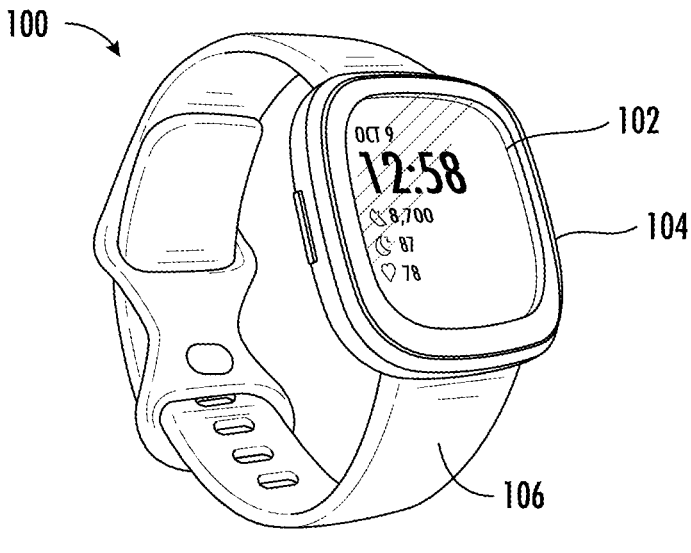
FIG. 1 illustrates an example wearable computing device in accordance with example embodiments of the present disclosure.

Reference now will be made in detail to embodiments, one or more examples of which are illustrated in the drawings. Each example is provided by way of explanation of the embodiments, not limitation of the present disclosure. In fact, it will be apparent to those skilled in the art that various modifications and variations can be made to the embodiments without departing from the scope or spirit of the present disclosure. For instance, features illustrated or described as part of one embodiment can be used with another embodiment to yield a still further embodiment. Thus, it is intended that aspects of the present disclosure cover such modifications and variations.

Generally, the present disclosure is directed towards systems for grouping users who have chosen to participate into one of a plurality of menstrual cycle groups based on data provided by and/or collected from those users. In some examples, a wearable computing device can include one or more sensors that can measure one or more physiological signals associated with the user. Based on the physiological signals gathered from the one or more sensors, the wearable computing device can determine biometric data for one or more users. For example, the biometric data can be one or more of: sleep data, activity data, and heart rate or heart rate variability data associated with the user. The biometric data can also be gathered from sources other than sensors. For example, a user can give permission to a data gathering system to access data associated with the user's health from a third-party source, an application on the wearable computing device, or another computing device associated with the user.

Furthermore, the wearable computing device can enable a user to submit information about their menstrual cycle (e.g., via an interactive touch screen). For example, the user can report the beginning and ending of one or more phases (e.g., the menstruation phase) of their menstrual cycle. It should be noted that while this disclosure primarily discusses menstrual cycle data submitted by a user, menstrual cycle data can also be automatically determined based on sensor data. For example, the sensor data can be used to determine hemoglobin levels and/or water retention levels. In other examples, the sensor data can estimate a user's internal or external temperature. These factors can be used to automatically determine some menstrual cycle data for a user.

The biometric data gathered from sensors and the menstrual cycle data submitted by users can be analyzed to determine a plurality of menstrual cycle groups into which users can be classified based on the biometric data, the menstrual cycle data, and correlations between the biometric data and the menstrual cycle data. For example, a cluster generation system can employ a clustering algorithm (e.g., K-means clustering) to cluster existing users based on previously submitted (or gathered) biometric and menstrual cycle data. In some examples, the clusters can be determined in an unsupervised manner. These clusters can be used to generate one or more menstrual cycle groups into which users can be classified.

In some implementations, the clustering process can include generating feature data for each user from the biometric data and the menstrual cycle data. The features can be directly taken from the biometric data and the menstrual cycle data or can be generated by correlating or otherwise combining the biometric data and the menstrual cycle data. Thus, some example features can describe correlations between the menstrual cycle data and the biometric data. As another example, the features can be cyclical features that describe cyclical patterns exhibited by the biometric data. For example, the menstrual cycle data can be used to extract, identify, or ascertain cyclical patterns within the biometric data that have a frequency that is based on or corresponds to the menstrual cycles of the user. The feature data can be used to determine the menstrual cycle groups and/or assign a user to one of the menstrual cycle groups.

Thus, the clustering algorithm can generate a plurality of menstrual cycle groups, each menstrual cycle group being associated with specific characteristics of biometric data, the menstrual cycle data, and/or correlations between the biometric data and the menstrual cycle data. In one specific example, the clustering algorithm can group users into five different menstrual cycle groups based on the regularity of their menstrual cycles and the degree to which the biometric data gathered from them (e.g., sleep data and heart rate data) is affected by one or more phases of their menstrual cycle. In other examples, users can also be clustered based on other factors, including, but not limited to age, medical conditions (when the user chooses to supply this information), the onset of menopause/perimenopause, and so on). Thus, the groups or clusters can be grouped along a plurality of different axes.

The regularity of a user's menstrual cycle can be represented by determining the amount of time (e.g., in days or hours) that a user takes to pass through each phase of their menstrual cycle. The amount of time can be measured over several complete menstrual cycles and the standard deviation can be calculated (e.g., the amount the length of the menstrual cycle varies by on average). A user with a low standard deviation (e.g., less than 2.0) can be determined to be more regular than a user with a high standard deviation. Another measure of regularity can be the difference between the longest menstrual cycle in the current data for the user and the shortest menstrual cycle in the current data for the user.

One biometric measure can be to determine an amount of change of an average heart rate or resting heart rate during a specific phase of the user's menstrual cycle. For example, the cluster generation system can determine whether the user's average heart rate decreases during the menstruation phase of the user's menstrual cycle. The biometric data can be separated into phase groups based on the cyclical pattern of the user's menstrual cycle. If the average heart rate of the user is lower during the sections of time associated with the menstruation of the user's relative to the average heart rate during the sections of time associated with other phases of the menstruation cycle, the cluster generation system can generate feature data indicating that the user's biometric data is affected by the user's menstrual cycle. In some examples, the biometric data can be analyzed longitudinally, such that patterns can be identified over multiple repetitions of the user's menstrual cycle.

Once a cluster generation system has generated one or more menstrual cycle groups, users can choose to allow the wearable computing device to use the user's biometric data and the menstrual cycle data to identify the menstrual cycle group into which the user best fits based on the feature value or ranges of values that are associated with each menstrual cycle group. In response, a cycle group determination system can determine which menstrual cycle group a respective user should be grouped into based on biometric and menstrual cycle data associated with the respective user.

Once the menstrual cycle group for the user has been determined, information associated with that group can be displayed to a user. Specifically, the wearable computing device can display information about the menstrual cycle group for the user including, but not limited to, the percentage of other users that are classified in that group, and information or advice that may be useful to overcome challenges faced by the user and other members of the user's particular menstrual cycle group.

In a specific example, a user may request that their wearable computing device determine the menstrual cycle group associated with the user. The wearable computing device can, in response to the request, access menstrual cycle data submitted by the user and data associated with one or more biometric indicators (e.g., information about the user's sleep sessions, information about the user's average resting heart rate, information about the user's activity over time, and information about the user's heart rate variability). A user who has a very regular menstrual cycle and sees an increase in sleep length during a particular phase of their menstrual cycle can be grouped into a menstrual cycle group with other users that share similar characteristics. The wearable computing device can access information about the menstrual cycle group including, but not limited to, the number of other users or percentage of other users that are in that menstrual cycle group, resources and advice that would be useful for members of the group, and access to discussion groups or other support areas that may be useful to the user. This information can be provided to the user upon request in a display associated with the wearable computing device. This information can also be stored in a user profile associated with the user.

More specifically, a wearable computing device can include any computing device that is integrated into an object that is meant to be worn by a user. For example, wearable computing devices can include, but are not limited to, smartwatches, fitness bands, computing devices integrated into jewelry such as smart rings or smart necklaces, computing devices integrated into items of clothing such as jackets, shoes, and pants, and wearable glasses with computing elements included therein. In some examples, a wearable computing device can include one or more sensors intended to gather information based on physiological signals with the permission of the user that is wearing the wearable computing device.

In some examples, the wearable computing device can include one or more sensors. The one or more sensors can include an accelerometer that can measure the movement of a user along three axes (e.g., x, y, and z dimensions). In some examples, the one or more sensors can include a heart rate sensor that determines a heart rate of the user. Other sensors can be used to measure other physiological data associated with the user.

In some examples, the biometric data can be detected by a device other than the wearable computing device. For example, a home computing device can include laser sensors to detect a user's movement or breathing rate. This information can be provided, with the user's permission, to the wearable computing device (or a server computing system associated with the wearable computing device) for analysis.

In some examples, the wearable computing device can transmit the sensor data to a server system for analysis. Additionally, or alternatively, the analysis can be performed at the wearable computing device. Thus, a group determination system can be enabled or executed at one or more of the wearable computing devices, a remote server system, or another computing system that can perform analysis of the sensor data and communicate with the wearable computing device to receive the sensor data.

In some examples, a user can submit menstrual cycle data via the wearable computing device. For example, a user can submit the time at which particular phases of the menstrual cycle begin and/or end. In some examples, the wearable computing device includes an application that is configured to allow a user to submit information about their menstrual cycle. In some examples, the user can also submit information about any specific details about one or more phases of their menstrual cycle (e.g., the severity of symptoms and so on).

Given the personal nature of the data described herein, it is contemplated that numerous techniques may be used to preserve privacy interests of the user. In some examples, as noted above, menstrual cycle data is only captured and stored on the user computing device if the user explicitly permits such capture and storage. Stored menstrual cycle data is stored securely (e.g., using cryptographic methods) to ensure the privacy of the user's data. Similarly, such data may only be used for training or improving classification models if the user explicitly permits it. Once the user gives permission, any user data optimally is anonymized to remove any user identifiable information. As a result, the data is not intended to be associated with any specific user, unless explicitly authorized by the user, and the user's privacy may be maintained even when the data is later used to train or improve a model. In addition, the storage of or use of any data, as well as potential responses to government requests for data will be in compliance with any applicable privacy laws to ensure user data is treated with the utmost security and the user's privacy is maintained. While some or all of the preceding techniques may be used to preserve a user's privacy, additional techniques may be used in furtherance of protecting the privacy of the data involved in the approaches described herein.

In some examples, a group determination system can access historical data from many users, including menstrual cycle data submitted by those users as well as biometric data collected via sensors from those users. For example, the cluster generation system can access meter cycle data and biometric data from a significant number of users (e.g., 50,000 users). The cluster generation system can use an algorithm to determine one or more groups based on the data from the 50,000 users. In some examples, the cluster generation system can use an unsupervised algorithm (such as K-means clustering) to group the users into a plurality of menstrual cycle groups. In some examples, the plurality of menstrual cycle groups can correspond to a plurality of different correlations between the menstrual cycle data and the biometric data.

The menstrual cycle data can include information about the regularity of the user's menstrual cycle (range of cycle length, mean cycle length, and cycle standard deviation). In some examples, the biometric data can include information that represents the average resting heart rate (RHR) of the user. The biometric data can also include data associated with the sleep of the user (e.g., length of sleep sessions and/or quality of sleep) based on movement from a movement sensor.

The cluster generation system can determine whether the biometric data (e.g., sleep data, resting heart rate data, and so on) exhibits changes based on the phase of the user's menstrual cycle. In some examples, some users consistently experience changes in one or more biometric measures during one or more phases of their menstrual cycle while other users experience little to no change regardless of the phase of the menstrual cycle.

The cluster generation system can generate a plurality of clusters by grouping users based on the regularity of their menstrual cycle and whether the user's biometric data exhibits change during one or more phases of the menstrual cycle. Once the clusters have been generated by the cluster generation system, the group determination system can determine which cluster (or group) a particular user should be included in.

In some examples, the menstrual cycle groups are associated with a particular theme or group name. The theme or group name can enable users to understand aspects of their menstrual cycle group without relying on displaying the exact underlying data that resulted in the cycle group determination system classifying the user into a particular menstrual cycle group. For example, menstrual cycle groups can be associated with themes such as types of geographies such as forests, beaches, coral reefs, and so on. Each specific group name can be associated with one or more characteristics of the menstrual cycle group.

Once the menstrual cycle group of a particular user has been determined, the user can be presented with information about their cycle group and or the theme of the cycle group. For example, if a particular user is determined to be in a menstrual cycle group associated with very regular menstrual cycle phases and changes in sleep patterns during a particular phase of the menstrual cycle, this information can be presented to the user, along with any additional information that may be helpful. The user can also be presented with an indication of the approximate percentage of the population that also falls within that menstrual cycle group.

In some examples, the determined menstrual cycle group can be used to select a particular ovulation prediction model for user when generating ovulation prediction data and or fertility data for a specific user.

Embodiments of the disclosed technology provide a number of technical effects and benefits, particularly in the areas of wearable computing devices. In particular, embodiments of the disclosed technology provide improved techniques for more effectively communicating useful health information to a user. For example, utilizing embodiments of the disclosed technology, a wearable computing device can use sensors included in the wearable computing device, combined with data submitted by the user, to accurately group users based on their menstrual cycle. Determining a useful menstrual cycle group for a user can ensure the user receives useful and accurate information associated with their particular menstrual cycle patterns which can improve health outcomes more generally as well has improving the users overall experience with the wearable computing device. Furthermore, this effect is accomplished with significantly lower cost than would be expected if such a task were to be accomplished using machines and processes build specifically for this purpose. As such, the disclosed embodiments enable additional functionality without significantly increasing the total cost of a wearable device.

With reference now to the figures, example aspects of the present disclosure will be discussed in greater detail.

FIG. 1 depicts the front view of an example wearable computing device 100 according to example embodiments of the present disclosure. In one embodiment, the wearable computing device 100 may be a wristband, a bracelet, a wristwatch, an armband, a ring placed around a digit of the user, or other wearable products that may be equipped with sensors as described in the present disclosure. In an example embodiment, the wearable computing device 100 is configured with a display 102, a device housing 104, a band 106, and one or more sensors. In an embodiment, the display 102 can be configured to present to a user data relating to the user's skin temperature, heart rate, sleep state, electroencephalogram, electrocardiogram, electromyography, electrooculogram, and other physiological data of the user (e.g., blood oxygen level). The display 102 can also be configured to convey data from additional ambient sensors contained within the wearable computing device 100. Example information conveyed on the display 102 from these additional ambient sensors can include the positioning, altitude, and weather of a location associated with the user. The display 102 can also convey data regarding the motion of the user (e.g., whether the user is stationary, walking, and/or running).

In an example embodiment, the display 102 can be configured to receive data input by the user. In an embodiment, a user can, by input on the display, request that the wearable computing device 100 generate additional data for display to the user (e.g., menstrual cycle group data). In response, the display can present instructions to the user to obtain the data requested (e.g., enter data associated with the user's menstrual cycle data). In some examples, the wearable computing device 100 can display instructions to the user (e.g., display "please hold your finger against a sensor for 10 seconds").

In an example embodiment, the device housing 104 can be configured to contain one or more sensors described in the present disclosure. Example sensors contained by the device housing 104 can include motion sensors (e.g., accelerometer), a pulse oximeter, an IR motion sensor, skin temperature sensors, internal device temperature sensors, location sensors (e.g., GPS), altitude sensors, heart rate sensors, audio sensors, pressure sensors, gyroscopes, environmental sensors (e.g., bedside ultrasounds sensors), and other physiological sensors (e.g., blood oxygen level sensors). In an embodiment, the device housing 104 can also be configured to include one or more processors. The band 106 can be configured to secure the wearable computing device 100 around an arm of the user by, for example, connecting ends of the band 106 with a buckle, clasp, or another similar securing device, thereby allowing the wearable computing device 100 to be worn by the user.

Figure 2:
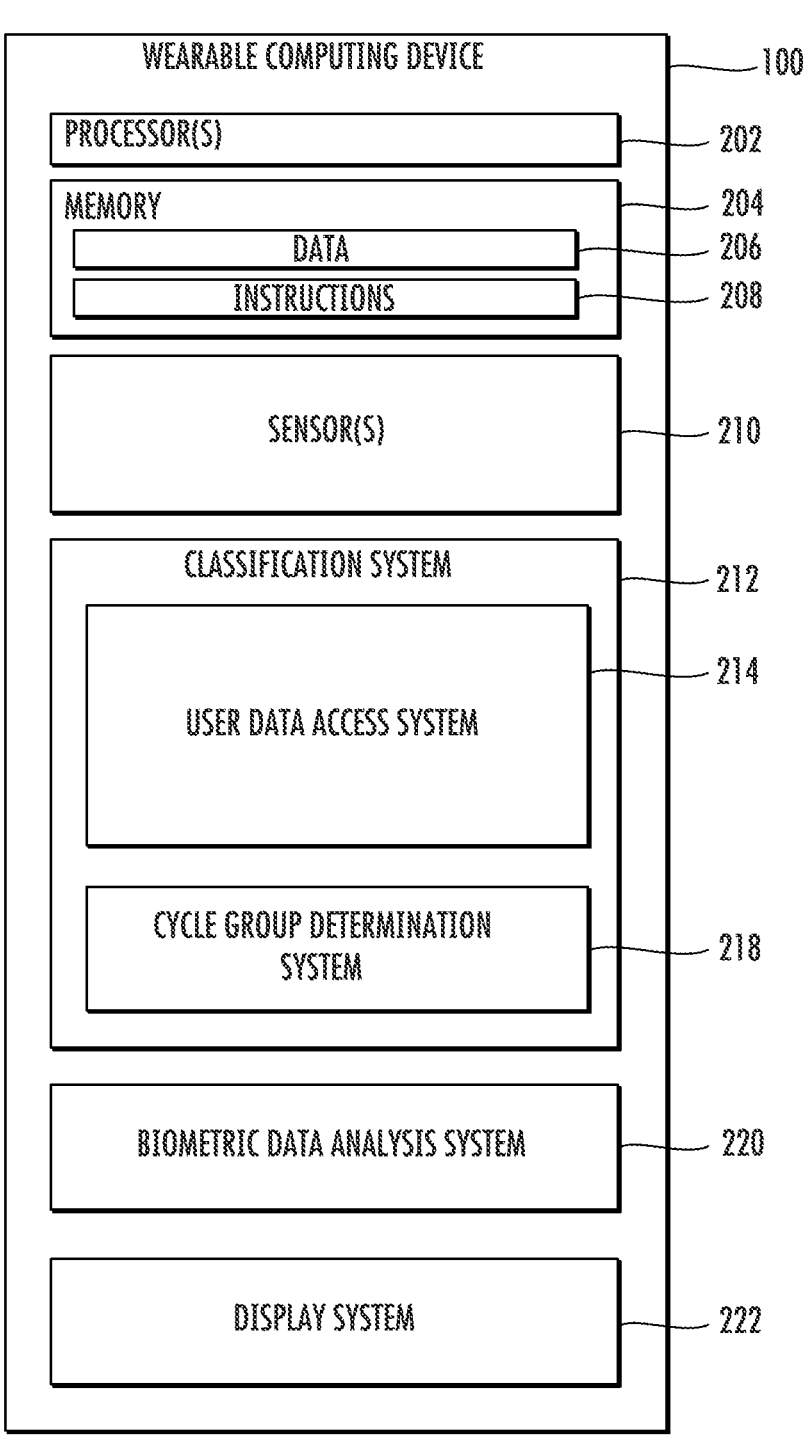
FIG. 2 illustrates a block diagram of an example computing environment that includes a wearable computing device having a sensor in accordance with example embodiments of the present disclosure.

FIG. 2 illustrates an example computing environment including a wearable computing device 100 in accordance with example embodiments of the present disclosure. In this example, the wearable computing device 100 can include one or more processors 202, memory 204, one or more sensors 210, a classification system 212, a biometric data analysis system 220, and a display system 222.

In more detail, the one or more processors 202 can be any suitable processing device that can be embedded in the form factor of a wearable computing device 100. For example, such a processor 202 can include one or more of: one or more processor cores, a microprocessor, an application-specific integrated circuit (ASIC), a FPGA, a controller, a microcontroller, etc. The one or more processors 202 can be one processor or a plurality of processors that are operatively connected. The memory 204 can include one or more non-transitory computer-readable storage mediums, such as RAM, ROM, EEPROM, EPROM, flash memory devices, etc., and combinations thereof.

In particular, in some devices, memory 204 can store instructions for implementing the classification system 212, the biometric data analysis system 220, and/or the display system 222. Thus, the wearable computing device 100 can implement the classification system 212, the biometric data analysis system 220, and/or the display system 222 to execute aspects of the present disclosure.

It will be appreciated that the term "system" can refer to specialized hardware, computer logic that executes on a more general processor, or some combination thereof. Thus, a system can be implemented in hardware, application specific circuits, firmware, and/or software controlling a general-purpose processor. In one embodiment, the system can be implemented as program code files stored on the storage device, loaded into memory, and executed by a processor or can be provided from computer program products, such as computer-executable instructions, that are stored in a tangible computer-readable storage medium such as RAM, hard disk or optical or magnetic media.

Memory 204 can also include data 206 and instructions 208 that can be retrieved, manipulated, created, or stored by the one or more processor(s) 202. In some example embodiments, such data can be accessed and used as input to the classification system 212, the biometric data analysis system 220, and/or the display system 222. In some examples, the memory 204 can include data used to perform one or more processes and instructions that describe how those processes can be performed.

In some examples, the wearable computing device 100 can include one or more sensors 210. For example, the sensors 210 can include, but are not limited to, one or more of: motions sensors (e.g., accelerometers), a pulse oximeter, an IR motion sensor, skin temperature sensors, internal device temperature sensors, location sensors (e.g., GPS), altitude sensors, heart rate sensors, audio sensors, pressure sensors, humidity sensors, and other physiological sensors (e.g., blood oxygen level sensors).

In some examples, the one or more sensors 210 can detect the movement of a user and provide motion data representing the movement to the wearable computing device 100. For example, an accelerometer can measure the movement of a user across three axes. For example, the accelerometer can measure the X, Y, and Z axes. Thus, as a user moves the accelerometer can generate data representing the movement and provide it to the wearable computing device 100. In another example, a heartbeat sensor can measure a user's heartbeat over a period to determine an average heart rate. Similarly, the heart rate sensor can be used to determine a resting heart rate (RHR) for a user. Other sensors, such as an IR laser sensor, a pulse oximeter, and so on can be used to determine the movement, activity level, or other physiological data associated with a user.

The sensor data generated by the sensors 210 can be transmitted to the biometric data analysis system 220. The biometric data analysis system 220 can use one or more signals produced by the one or more sensors 210 to determine biometric information about one or more biometric indicators. For example, the motion data produced by an accelerometer can be used to determine the average amount of movement that a user makes in a particular period of time. For example, the biometric data analysis system 220 can determine the amount of movement by a user during a minute increment. The amount of movement determined for the user can be used to estimate whether the user is asleep at a particular moment. In some examples, the movement sensor data can be used to determine when a user's sleep session starts and when it ends. In addition, the movement data can be used to identify one or more sleep stages during the current sleep session. The sleep data can be stored for use by the classification system 212.

The biometric data analysis system 220 can also determine other information like the heart rate of the user on average over a period or the average resting heart rate of a user. In some examples, the biometric data analysis system 220 can access biometric or health associated data from sources other than the directly from the one or more sensors. For example, a user can directly supply additional biometric data if the user so chooses. In addition, the user can supply or give permission to the biometric data analysis system 220 to access medical or clinical records associated with the user. Such records can, with the specific permission of the user, allow the biometric data analysis system 220 to access information about the user's health, including, but not limited to, information about the user's blood pressure, hemoglobin levels, average resting heart rate, heart rate variability, medical conditions, and so on. Such data can be useful in grouping the users and/or interpreting other data gathered from the user.

Data about one or more biometric indicators (e.g., information about the user's sleep sessions, information about the user's average resting heart rate, information about the user's activity over time, and information about the user's heart rate variability), can be transmitted to the classification system 212.

The classification system 212 can include a user data access system 214 and a cycle group determination system 218. The user data access system 214 can access biometric data from the biometric data analysis system 220 and the user supplied menstrual data. For example, the user supplied menstrual data can include data associated with a user's menstrual cycle. In some examples, the wearable computing device 100 can include an application that allows the user to enter data associated with their cyclical menstrual cycle.

In some examples, the user data access system 214 can process the various data sources it receives (e.g., data generated by the biometric data analysis system 220 and data supplied by the user associated with their cyclical menstrual cycle) to generate one or more features associated with the users. In some examples, the data supplied by the user associated with the user's cyclical menstrual cycle can be interpreted based on data on the user's general health or medical conditions). For example, if a user has chosen to supply information about a specific medical condition (e.g., pregnancy, menopause, PCOS, and so on), the user data access system 214 can interpret the cyclical menstrual cycle data in light of that information. For example, if a user was pregnant for a period, the menstrual cycle data from that period (or the lack of menstrual data during that period) can be disregarded when evaluating a user's regularity.

The features can be directly taken from the biometric data and the menstrual cycle data or can be generated by correlating or otherwise combining the biometric data and the menstrual cycle data. In some examples, the features can be normalized such that the feature values for all features fall within a normalized range (e.g., between 0 and 1). Thus, some example features can describe correlations between the menstrual cycle data and the biometric data. As another example, the features can be cyclical features that describe cyclical patterns exhibited by the biometric data. For example, the menstrual cycle data can be used to extract, identify, or ascertain cyclical patterns within the biometric data that have a frequency that is based on or corresponds to the menstrual cycles of the user. In some examples, the feature data can be generated by preprocessing the data. For example, the heart rate data can be represented as a heart rate time series. In some examples a Kalman filter can be applied to the time series to generate feature data for use as input to a model.

In some examples, feature data can include measures of heart rate variability during a particular time of day. For example, the user's heart rate at night can be compared based on the phase of the user's menstrual cycle to generate feature data. Similarly, the heart rate change can be measured during only a specific sleep phase.

In some examples, the feature data can include activity metrics (e.g., the average or total amount of activity associated with a user during a particular period (e.g., a day, an hour, and so on). For example, the feature data can determine the amount of time the user spends in a high activity zone in a particular day. Another potential activity metric is number of steps taken. These metrics can be used to generate activity feature data that can be compared to determine whether a change occurs consistently during one or more phases of the user's menstrual cycle.

In some examples, feature data can also be derived based on a sleep score, a readiness score, the percentage of a user's night in which their heart rate is below an average resting heart rate, and so on. In some examples, any physiological data that can be measured by a sensor can be compared to the cyclical menstrual cycle data to determine whether or not a consistent change is identifiable.

In some examples, biometric data can be altered by factors other than the user's menstrual cycle and the biometric data can be adjusted to mitigate these other factors. For example, the user's sleep data can be affected by the 7-day work cycle. As such, the data from weekend days can be excluded from the analysis to ensure that it does not bias the analysis.

In some examples, feature data can represent the average amount of sleep the users gets for each day. This can be compared against the cyclical menstrual cycle data to determine whether any phase of the menstrual cycle consistently changes the length of the user's sleep.

The generated feature data can be used as input to the cycle group determination system 218. In some examples, the cycle group determination system 218 can determine the appropriate menstrual cycle group for a user based on previously determined menstrual cycle groups of users. Menstrual cycle groups can have associated range values for the feature data such that users with feature data values that fall within a certain range are included in a particular group. In a very simple example, two features can be used. Thus, a first group can include all users with a first feature value between 0 and 0.5 and a second feature value of 0.2 and 0.6. A second group can include users with a first feature value between 0 and 0.5 and a second feature value between 0.6 and 1.0. Other groups can be associated with other ranges of feature values. Thus, a user can be classified into a particular group based on their associated feature value ranges.

In some examples, the cycle group determination system 218 can include a machine learning model that takes feature data as inputs and outputs a group classification. Thus, the cycle group determination system 218 can access data provided by the biometric data analysis system 220 and the user data access system 214 and convert it into feature data for input to the machine learning model. In some examples, such a machine learning model could also output a confidence value associated with a group classification indicating how confident the machine learning model is that the user is correctly classified.

Once the user has been classified into a particular menstrual cycle group from a plurality of one or more menstrual cycle groups, the classification system 212 can provide group identification data to the display system 222. The display system 222 can present the data identifying the menstrual cycle group into which the user has been classified. The data identifying the menstrual cycle group can include a theme or group name of the group, information about the menstrual cycle characteristics of users who fall within the group, the percentage of users within the group, and other helpful information.

Figure 3:
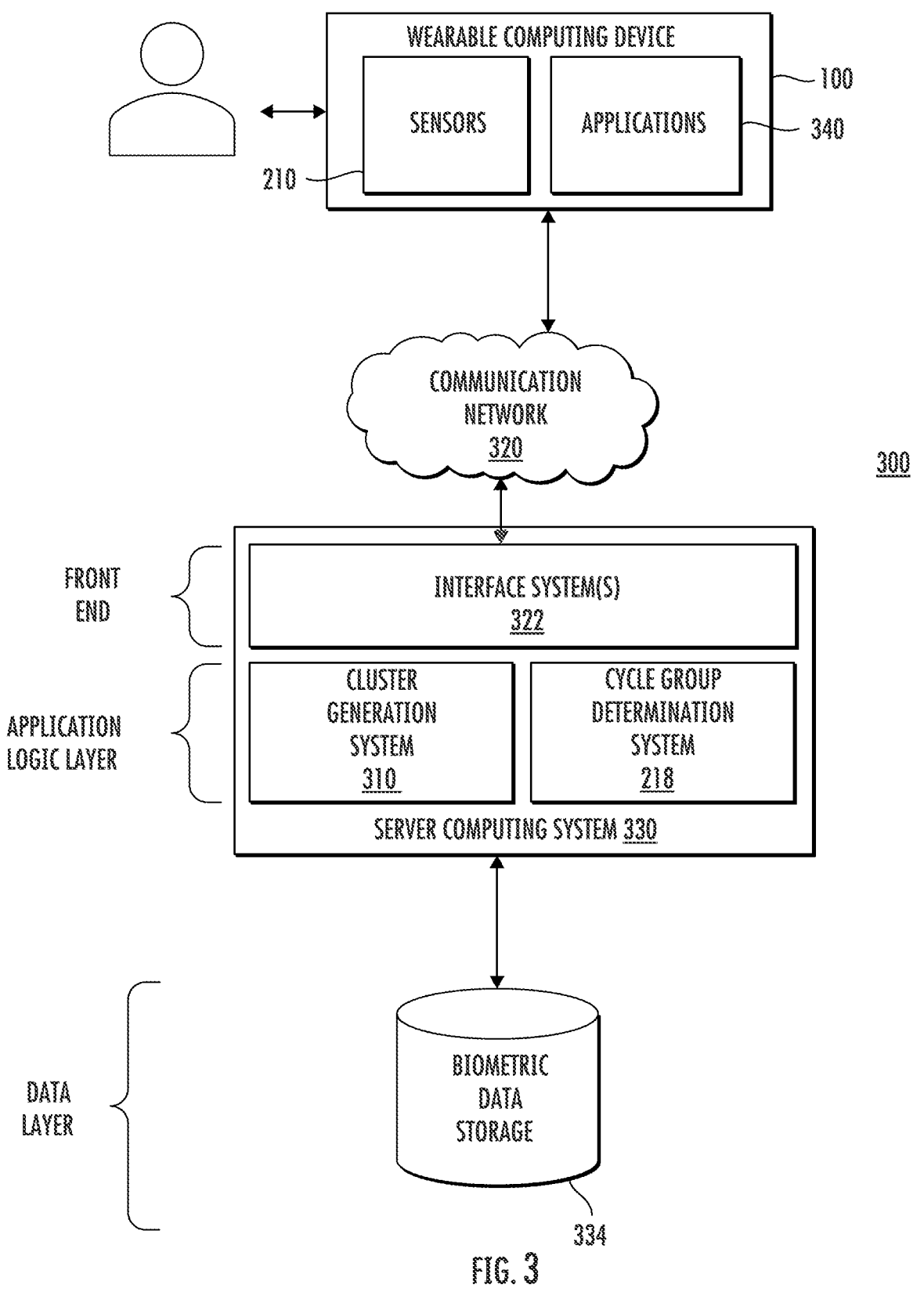
FIG. 3 illustrates a block diagram of a computing environment including a wearable computing device connected to a server computing system via a network in accordance with example embodiments of the present disclosure.

FIG. 3 depicts an example client-server environment according to example embodiments of the present disclosure. The client-server system environment 300 includes one or more wearable computing devices 100 and a server computing system 330. One or more communication networks 320 can interconnect these components. The communication networks 320 may be any of a variety of network types, including local area networks (LANs), wide area networks (WANs), wireless networks, wired networks, the Internet, personal area networks (PANs), or a combination of such networks.

A wearable computing device 100 can include, but is not limited to, smartwatches, fitness bands, computing devices integrated into jewelry such as smart rings or smart necklaces, computing devices integrated into items of clothing such as jackets, shoes, and pants, and wearable glasses with computing elements included therein. In some examples, a wearable computing device 100 can include one or more sensors intended to gather information with the permission of the user that is wearing the wearable computing device 100.

In some examples, the wearable computing device 100 can connect to another computing device, such as a personal computer (PC), a laptop, a smartphone, a tablet, a mobile phone, an electrical component of a vehicle, or any other electronic device capable of communication with the communication network 320. A wearable computing device 100 can include one or more application(s) 340 such as search applications, communication applications, navigation applications, productivity applications, game applications, word processing applications, or any other applications. The application(s) 340 can include a web browser. The wearable computing device 100 can use a web browser (or other application) to send and receive requests to and from the server computing system 330. The application(s) 340 can include an application that enables the user to log information associated with their menstrual cycles, including the beginning and ending of one or more phases of the menstrual cycle and any other accompanying information (e.g., which symptoms occur and what strength).

In some examples, the wearable computing device 100 can include one or more sensors that can be used to determine the movement of a user at a particular time. For example, the sensors 210 can include, but are not limited to, motion sensors (e.g., accelerometer), a pulse oximeter, an IR motion sensor, skin temperature sensors, internal device temperature sensors, location sensors (e.g., GPS), altitude sensors, heart rate sensors, audio sensors, pressure sensors, and other physiological sensors.

As shown in FIG. 3, the server computing system 330 can generally be based on a three-tiered architecture, consisting of a front-end layer, application logic layer, and data layer. As is understood by skilled artisans in the relevant computer and Internet-related arts, each component shown in FIG. 3 can represent a set of executable software instructions and the corresponding hardware (e.g., memory and processor) for executing the instructions. To avoid unnecessary detail, various components and engines that are not germane to conveying an understanding of the various examples have been omitted from FIG. 3. However, a skilled artisan will readily recognize that various additional components and engines may be used with a server computing system 330, such as that illustrated in FIG. 3, to facilitate additional functionality that is not specifically described herein. Furthermore, the various components depicted in FIG. 3 may reside on a single server computer or may be distributed across several server computers in various arrangements. Moreover, although the server computing system 330 is depicted in FIG. 3 as having a three-tiered architecture, the various example embodiments are by no means limited to this architecture.

As shown in FIG. 3, the front end can consist of an interface system(s) 322, which receives communications from one or more wearable computing devices 100 and communicates appropriate responses to the wearable computing devices 100. For example, the interface system(s) 322 may receive requests in the form of Hypertext Transfer Protocol (HTTP) requests, or other web-based, application programming interface (API) requests. The wearable computing devices 100 may be executing conventional web browser applications or applications that have been developed for a specific platform to include any of a wide variety of mobile devices and operating systems.

As shown in FIG. 3, the data layer can include a biometric data storage 334. The biometric data storage 334 can include data gathered by sensors from a plurality of users. Specifically, a motion sensor can be used to detect the motion of the user and derive various information about the user (e.g., when the user is asleep, when the user is active and the level of activity, and so on). In addition, a heart rate sensor can measure a user's heart rate at a particular moment or generate average heart rate data over a period. The data gathered from a plurality of users can be stored for later use with the approval and/or permission of the user.

The application logic layer can include application data that can provide a broad range of other applications and services that allow users to access or receive geographic data for navigation or other purposes. The application logic layer can include a cluster generation system 310 and a cycle group determination system 218.

The cluster generation system 310 can receive via the information interface system 322 and/or access data from the biometric data storage 334. The cluster generation system 310 can generate a plurality of clusters by grouping users based on one or more features generated based on sensor data, menstrual cycle data, and correlations between them. In some examples, the features can be directly taken from the biometric data and the menstrual cycle data or can be generated by correlating or otherwise combining the biometric data and the menstrual cycle data. Thus, some example features can describe correlations between the menstrual cycle data and the biometric data. As another example, the features can be cyclical features that describe cyclical patterns exhibited by the biometric data.

Once feature data has been generated for each user (based on historical data submitted by a large group of users), the cluster generation system 310 can use a clustering algorithm to generate a plurality of menstrual cycle groups. The menstrual cycle groups can be generated such that each menstrual cycle group is associated with specific characteristics of biometric data, the menstrual cycle data, and/or correlations between the biometric data and the menstrual cycle data. In one specific example, the clustering algorithm can group users into five different menstrual cycle groups based on the regularity and length of their menstrual cycles and the degree to which their sleep data and heart rate data are affected by one or more phases of their menstrual cycle.

Once the cluster generation system 310 generates clusters for the plurality of users into a group of menstrual cycle groups, each with a group definition describing the specific feature values for users that are included in the group, the cycle group determination system 218 can use the group definitions to determine an appropriate menstrual cycle group for a particular user.

Thus, if a user associated with at wearable computing device 100 requests a determination to identify their associated menstrual cycle group, the wearable community device 100 can transmit data associated with the user (including sensor data and reported menstrual cycle data) to the server system 330. The server system 330 can then use the cycle group determination system 218 to identify which menstrual cycle group the user is most appropriately placed in. The cycle group identification can be transmitted back to the wearable computing device. The wearable computing device 100 can display that information to the user.

Figure 4:
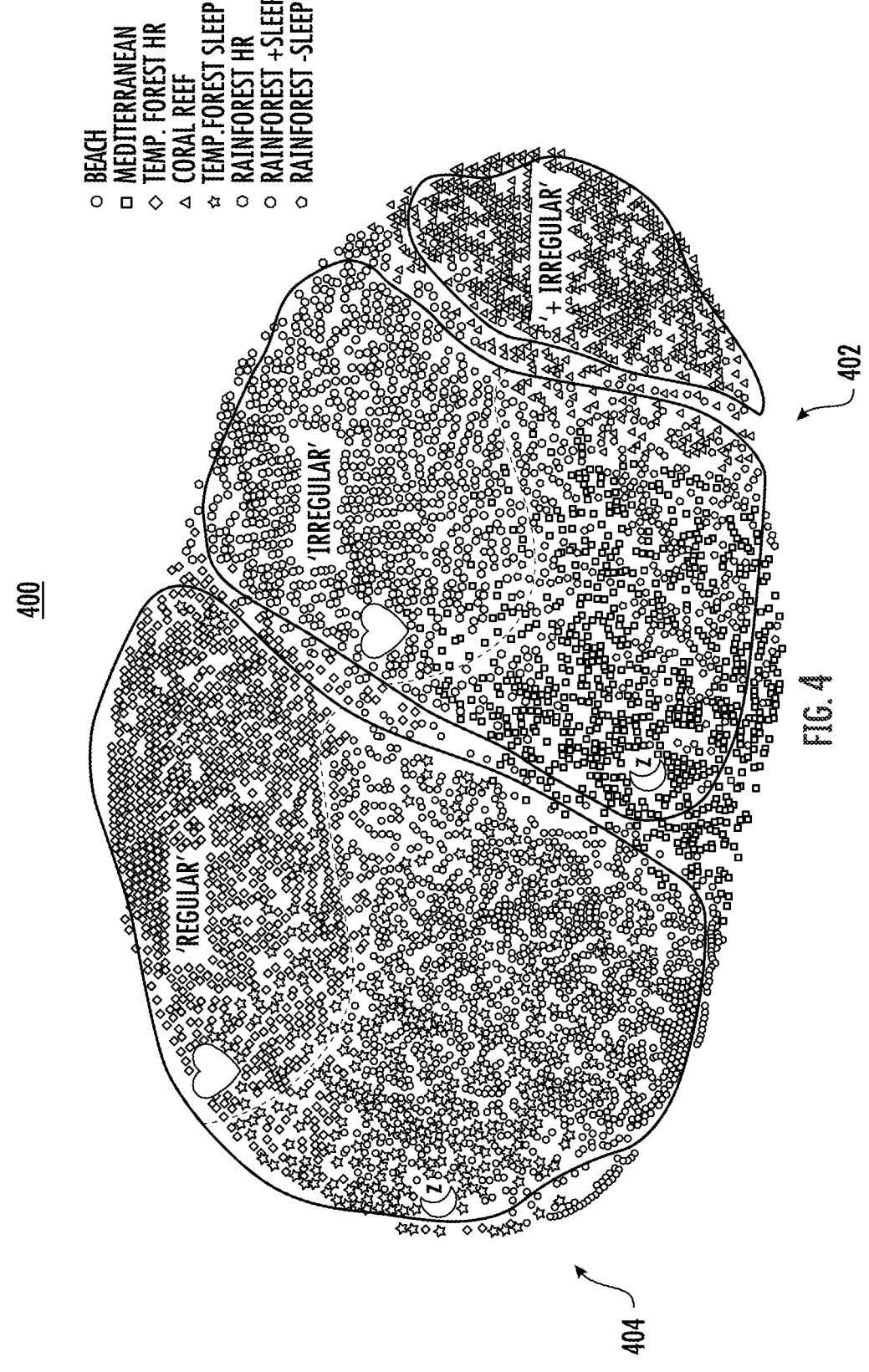
FIG. 4 is a diagram of example groups for cycler types in accordance with example embodiments of the present disclosure.

FIG. 4 is a diagram of example groups for cycler types in accordance with example embodiments of the present disclosure. This example, users are plotted on a graph 400 wherein each point is determined based on the regularity of the user's menstrual cycle and the degree to which biometric signals (e.g., heart rate and sleep data) are altered by one or more cycles of the users menstrual cycle. Thus, the X axis 402 is associated with the regularity of the user's menstrual cycle, and the Y axis 404 is associated with the changes to biometric data that occur when the user is in a particular phase of their menstrual cycle.

The cycle group determination system can use an unsupervised clustering algorithm (e.g., K-means clustering) to generate a plurality of clusters based on the data. In this example, the users can be clustered into five menstrual cycle groups. The five groups can consist of a first group including users with a regular menstrual cycle and no biometric changes, a second group including users with a regular menstrual cycle and biometric data changes, a third group including users with an irregular menstrual cycle and no biometric changes, a fourth group including users with an irregular menstrual cycle and biometric changes, and a fifth group including users with a very irregular menstrual cycle and no biometric changes.

Once the users have been clustered into specific menstrual cycle groups, the classification system can use the groupings to determine where a specific user should be grouped based on the feature data for the specific user. Thus, a plurality of users can be classified into respective menstrual cycle groups as the users request menstrual cycle group data. In some examples, the clustering can be periodically updated as new data is added to a repository of user biometric data and menstrual cycle data.

FIG. 5 illustrates an example user interface display associated with one or more cycle types in accordance with example embodiments of the present disclosure. In this example, a computing device (e.g., a smartphone) displays one or more menstrual cycle group theme labels and an accompanying description. These theme labels can be displayed to a user once the user has been classified into a particular menstrual cycle group.

For example, one specific menstrual cycle group can have a theme label of temperate forest 502. As displayed in the description, a user that has been grouped into the temporal forest menstrual cycle group 502 can have a regular menstrual cycle and have increased sleep length during the follicular phase of their menstrual cycle. In addition, the user interface also displays data indicating that 32% of users are grouped into the same menstrual cycle group.

Another displayed menstrual cycle group 504 can have a rainforest theme. In this example, the rainforest menstrual cycle group 504 can be associated with users who have less regular menstrual cycles with some changes in sleep length for the users in the group. For example, some users in the rainforest group can experience a 27% increase in sleep during the luteal phase while others in this group sleep 35% more in the follicular phase. In addition, the user interface can display that 28% of users are grouped into this group.

Another displayed example can be a menstrual cycle group with the theme of Mediterranean 506. Users in this group can have irregular menstrual cycles and no consistent identifiable changes in biometric data during their menstrual cycle. The user interface can also display that 14% of users fit into this group.

FIG. 6A illustrates a representation of data associated with a resting heart rate for a user and cycle information in accordance with example embodiments of the present disclosure. This graph shows the pattern of a user's resting heart rate represented over time (e.g., multiple menstrual cycles). The graph has sections associated with the menstruation phase of the user's menstrual cycle highlighted. This graph illustrates the process of identifying whether a biometric indicator (in this case resting heart rate) is consistently affected by one or more phases of the menstrual cycle.

As can be seen in this graph, the user's resting heart rate consistently decreases during the menstruation phase of the menstrual cycle. As a result, a classification system can determine that the user has at least one biometric indicator that is consistently affected by the specific phase of the user's menstrual cycle.

FIG. 6B illustrates a representation of data associated with a resting heart rate for a user and cycle information in accordance with example embodiments of the present disclosure. This graph shows the pattern of a user's resting heart rate represented over time (e.g., multiple menstrual cycles). The graph has sections associated with the menstruation phase of the user's menstrual cycle highlighted. As with the graph in FIG. 6A, this graph illustrates the process of identifying whether a biometric indicator (in this case resting heart rate) is consistently affected by one or more phases of the menstrual cycle.

As can be seen in this graph, the user's resting heart rate does not consistently change during the menstruation phase of the menstrual cycle (or any other phase). Instead, the changes in the user's resting heart rate are independent of the specific phase of the user's menstrual cycle in which the changes occur. As a result, a classification system can determine that the user's heart rate is not consistently affected by the specific phase of the user's menstrual cycle.

Figure 7A:
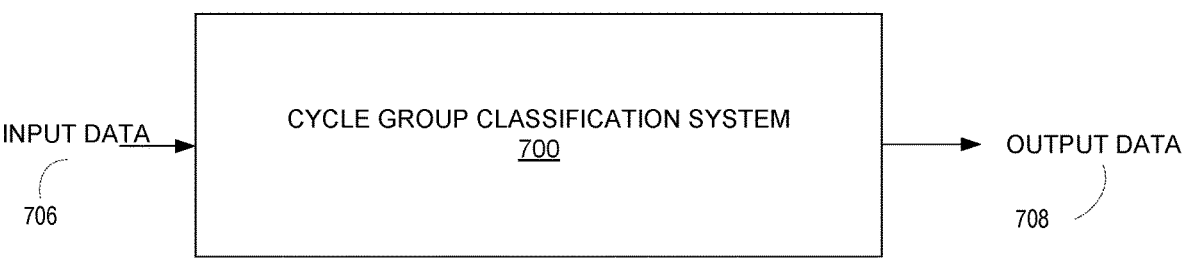
FIG. 7A depicts a block diagram of an example cycle group classification system according to example embodiments of the present disclosure.

FIG. 7A depicts a block diagram of an example cycle group classification system 700 according to example embodiments of the present disclosure. In this example, the cycle group classification system 700 can take user-specific biometric data and user specific menstrual cycle data provided by the user as input data 706. In some examples, the user-specific biometric data is gathered by sensors and includes movement data, heart rate data, and other data gathered by sensors that measure physiological signals. The user menstrual cycle data can include data submitted by the user including the start and stop of one or more phases of the menstrual cycle as well as any information about accompanying symptoms and their severity.

In some examples, the cycle group classification system 700 can generate feature data based on the input data from sensors and from user-submitted menstrual cycle data. In some examples, the feature data can represent one or more of the biometric data and or cycle data and or correlations between the two data.

Once the feature data has been generated, the cycle group classification system 700 can determine which menstrual cycle group the user should be placed into based on previously determined cycle group data ranges. In some examples, the cycle group classification system 700 can also generate a confidence value representing the degree to which the cycle group classification system 700 is confident that the user belongs in a particular menstrual cycle group. If the user is close to a boundary between two menstrual cycle groups, the cycle group classification system 700 can indicate both menstrual cycle groups and assign a confidence value to each. For example, the user may have a 70% confidence value associated with group one and a 30% confidence value associated with group two. In this example, the cycle group classification system 700 can select the group with the higher confidence value to present to the user.

The cycle group determination system 700 can generate output data 708 that represents the specific menstrual cycle group the user has been grouped into and or any confidence data generated as part of that process. The output data can be transmitted to the wearable computing device for display to a user.

Figure 7B:
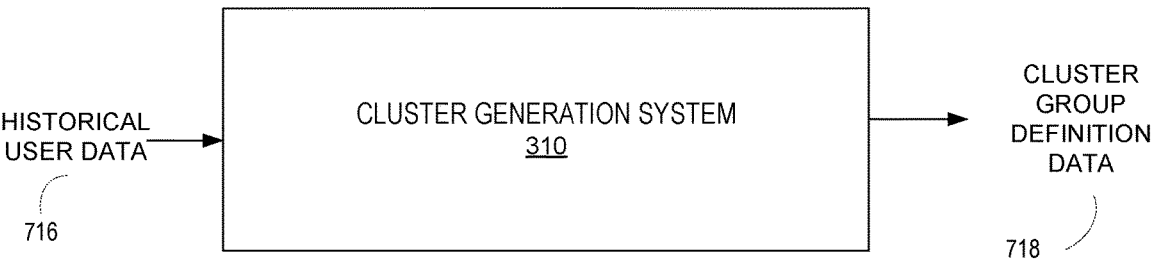
FIG. 7B depicts a block diagram of an example cluster generation system according to example embodiments of the present disclosure.

FIG. 7B depicts a block diagram of an example cluster generation system 310 according to example embodiments of the present disclosure. In this example, the cluster generation system 310 can take, as input, historical user data 716. The historical user data 716 can include data from a large number of users (e.g., 50,000 or more). This data can include biometric data and menstrual cycle data for these users. This data can be collected over time with the permission of the users and stored for analysis. The cluster generation system 310 can generate feature values from the historical user data. The feature data can be normalized and a clustering algorithm can be used to generate a plurality of cluster groups.

In some examples, the clustering algorithm can operate in an unsupervised manner. Example clustering algorithms can include a k-means clustering algorithm, a means-shift clustering algorithm, a density-based spatial clustering algorithm, Expectation-Maximization (EM) Clustering. Agglomerative hierarchical clustering algorithm, and/or any other clustering algorithm. In some examples, the number of clusters can be selected by a user. In other examples, the number of clusters is determined automatically determined by the algorithm itself.

Once the clusters have been generated, the cluster generation system 310 can output cluster group definition data 718. The cluster group definition data 718 can define the specific feature data ranges associated with each cluster.

FIG. 8 is a flowchart depicting an example process of determining a cycle group of a user in accordance with example embodiments of the present disclosure. One or more portion(s) of the method can be implemented by one or more computing devices such as, for example, the computing devices described herein. Moreover, one or more portion(s) of the method can be implemented as an algorithm on the hardware components of the device(s) described herein. FIG. 8 depicts elements performed in a particular order for purposes of illustration and discussion. Those of ordinary skill in the art, using the disclosures provided herein, will understand that the elements of any of the methods discussed herein can be adapted, rearranged, expanded, omitted, combined, and/or modified in various ways without deviating from the scope of the present disclosure. The method can be implemented by one or more computing devices, such as one or more of the computing devices depicted in FIGS. 1-3.

A computing device (e.g., wearable computing device 100 in FIG. 1) can be configured to perform a method for associating a user with a menstrual cycle cohort. The method can comprise obtaining, at 802, menstrual cycle data for the user. In some examples, the menstrual cycle data is determined based on data submitted by the user about the user's menstrual cycle. More specifically, the menstrual cycle data can include data representing a length of one or more phases of the menstrual cycle. For example, a user can use an application included on the computing device to indicate when one or more phases of the user's menstrual cycles begin and end as well as any symptoms associated the particular phase.

In some examples, the computing device 100 is a wearable computing device. Wearable computing devices can include smartwatches, fitness bands, computing devices included in clothing and/or jewelry, and so on. In some examples, the wearable computing device can include one or more sensors. The wearable computing device can be communicatively coupled with another computing device (e.g., a smartphone, laptop, personal computer, and so on) such that some or all of the processing occurs at a computing device remote from the wearable computing device.

The computing device 100 can detect, at 804, by one or more sensors included in the computing device, biometric data from the user. In some examples, the biometric data includes heartbeat data. For example, a heartbeat sensor can measure a user's heartbeat at a particular moment or generate an average over a period of item. In some examples, the heart rate data can be an average resting heart rate or a heart rate variability metric. The biometric data can include sleep data. In some examples, the sleep data can include the length of sleep sessions and quality of sleep based on movement from a movement sensor.

The computing device 100 can determine, at 806, based on the menstrual cycle data and the biometric data, a menstrual cycle group for the user from a plurality of menstrual cycle groups, wherein the plurality of menstrual cycle groups is generated by performance of a clustering algorithm that groups users into clusters based on correlations between the menstrual cycle data and the biometric data.

The menstrual cycle group determined for a particular user can be based, at least in part, on a regularity of the user's menstrual cycle. Regularity can be measured based on the consistency of the length of one or more phases of the user's menstrual cycle.

In some examples, the menstrual cycle group for a user can be based, at least in part, on changes that occur to biometric data of the user during one or more phases of the user's menstrual cycle. For example, the biometric data for a user can be correlated with the information associated with the user's menstrual cycle. The menstrual cycle data is cyclical, and the wearable computing device can determine whether any of the biometric data is consistently altered (e.g., higher or lower in amount or frequency) during a particular phase of the user's menstrual cycle. In some examples, changes to biometric data include one or more of a change in average heart rate, a change in sleep duration, and a change in sleep quality.

In some examples, the one or more phases can include a luteal phase, an ovulation phases, a follicular phase, and a menstruation phase. The changes in biometric data can be analyzed with respect to any of the phases of the user's menstrual cycle.

In some examples, the clustering algorithm can be performed in an unsupervised fashion. In some examples, the clustering algorithm comprises a K-means clustering algorithm. When the K-means clustering algorithm is run, a group determination system can select a particular number of clusters (e.g., the K in K-means). For example, the group determination system can, based on user input, select 8 groups. The clusters can also be combined after the clustering algorithm as needed. For example, eight clusters can be combined into five groups as needed.

In some examples, the computing device 100 can generate a plurality of features for the user from the menstrual cycle data and the biometric data, wherein at least some of the plurality of features describe correlations between the menstrual cycle data and the biometric data. The computing device 100 can classify the user into the menstrual cycle group from the plurality of menstrual cycle groups based on the features.

In some examples, the computing device 100 can generate a plurality of features for the user from the menstrual cycle data and the biometric data, wherein at least some of the plurality of features comprise cyclical features that describe cyclical patterns exhibited by the biometric data. The computing device 100 can classify the user into the menstrual cycle group from the plurality of menstrual cycle groups based on the features.

Once a menstrual group is determined for a particular user the computing device 100 can display, in a display associated with the computing device 100, data representing the determined menstrual cycle group for the user.

The technology discussed herein refers to sensors and other computer-based systems, as well as actions taken, and information sent to and from such systems. One of ordinary skill in the art will recognize that the inherent flexibility of computer-based systems allows for a great variety of possible configurations, combinations, and divisions of tasks and functionality between and among components. For instance, server processes discussed herein may be implemented using a single server or multiple servers working in combination. Databases and applications may be implemented on a single system or distributed across multiple systems. Distributed components may operate sequentially or in parallel.

While the present subject matter has been described in detail with respect to specific example embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A computer-implemented method for association of a user with a menstrual cycle cohort, the method comprising:

accessing, by a computing device, user data for a plurality of users;

generating, by the computing device, a plurality of menstrual cycle groups by performing a clustering algorithm that groups the plurality of users into clusters based on the user data for the plurality of users;

obtaining, by the computing device, menstrual cycle data for the user;

detecting, by one or more sensors included in the computing device, biometric data from the user;

determining, by the computing device based on the biometric data and the menstrual cycle data, a first value for a biometric indicator during a first menstrual cycle phase and a second value for the biometric indicator during a second menstrual cycle phase;

determining, by the computing device, a difference between the first value for the biometric indicator during the first menstrual cycle phase to the second value for the biometric indicator during the second menstrual cycle phase;

determining, by the computing device and based on the difference between the first value for the biometric indicator during the first menstrual cycle phase to the second value for the biometric indicator during the second menstrual cycle phase, a menstrual cycle group for the user from the plurality of menstrual cycle groups; and displaying, in a display associated with the computing device, data representing the determined menstrual cycle group for the user.

2. The computer-implemented method of claim 1, wherein the menstrual cycle data is determined based on data submitted by the user about the user's menstrual cycle.

3. The computer-implemented method of claim 1, wherein the menstrual cycle data includes data representing a length of one or more phases of a menstrual cycle.

4. The computer-implemented method of claim 1, wherein the biometric data includes heartbeat data.

5. The computer-implemented method of claim 1, wherein the biometric data includes sleep data.

6. The computer-implemented method of claim 1, wherein the menstrual cycle group for a user is based, at least in part, on a regularity of the user's menstrual cycle.

7. The computer-implemented method of claim 1, wherein the user data comprises biometric data and menstrual cycle data.

8. The computer-implemented method of claim 1, wherein the biometric indicator comprises one or more of a change in average heart rate, a change in sleep duration, and a change in sleep quality.

9. The computer-implemented method of claim 1, wherein the first menstrual cycle phase is one of a luteal phase or a follicular phase.

10. The computer-implemented method of claim 1, wherein the clustering algorithm is performed in an unsupervised fashion.

11. The computer-implemented method of claim 10, wherein the clustering algorithm comprises a K-means clustering algorithm.

12. The computer-implemented method of claim 1, wherein the computing device is a wearable computing device.

13. The computer-implemented method of claim 1, wherein determining, by the computing device and based on the difference between the difference between the first value for the biometric indicator during the first menstrual cycle phase to the second value for the biometric indicator during the second menstrual cycle phase, the menstrual cycle group for the user from the plurality of menstrual cycle groups further comprises:

generating a plurality of features for the user from the menstrual cycle data and the biometric data, wherein at least some of the plurality of features describe correlations between the menstrual cycle data and the biometric data; and classifying the user into the menstrual cycle group from the plurality of menstrual cycle groups based on the features.

14. The computer-implemented method of claim 1, wherein determining by the computing device and based on the difference between the difference between the first value for the biometric indicator during the first menstrual cycle phase to the second value for the biometric indicator during the second menstrual cycle phase, the menstrual cycle group for the user from the plurality of menstrual cycle groups further comprises:

generating a plurality of features for the user from the menstrual cycle data and the biometric data, wherein at least some of the plurality of features comprise cyclical features that describe cyclical patterns exhibited by the biometric data; and classifying the user into the menstrual cycle group from the plurality of menstrual cycle groups based on the features.

15. A system for determining a user's menstrual cycle group, the system comprising:

a computing system comprising one or more processors, one or more sensors, and a non-transitory computer-readable memory;

wherein the non-transitory computer-readable memory stores instructions that, when executed by the processor, cause the computing system to perform operations, the operations comprising:

accessing user data for a plurality of users;

generating a plurality of menstrual cycle groups by performing a clustering algorithm that groups the plurality of users into clusters based on the user data for the plurality of users;

obtaining menstrual cycle data for the user;

detecting, by the one or more sensors, biometric data from the user;

determining, based on the biometric data and the menstrual cycle data, a first value for a biometric indicator during a first menstrual cycle phase and a second value for the biometric indicator during a second menstrual cycle phase;

determining a difference between the first value for the biometric indicator during the first menstrual cycle phase to the second value for the biometric indicator during the second menstrual cycle phase;

determining, based on the difference between the first value for the biometric indicator during the first menstrual cycle phase to the second value for the biometric indicator during the second menstrual cycle phase, a menstrual cycle group for the user from the plurality of menstrual cycle groups; and providing for display data representing the determined menstrual cycle group for the user.

16. The system of claim 15, wherein the menstrual cycle data is determined based on data submitted by the user.

17. The system of claim 15, wherein the menstrual cycle data includes data representing a length of one or more phases of a menstrual cycle.

18. The system of claim 15, wherein the biometric data includes heartbeat data or sleep data.

19. The system of claim 15, wherein user data comprises biometric data and menstrual cycle data.

20. A non-transitory computer-readable medium storing instructions that, when executed by one or more computing devices, cause the one or more computing devices to perform operations, the operations comprising:

accessing, by the one or more computing devices, user data for a plurality of users;

generating, by the one or more computing devices, a plurality of menstrual cycle groups by performing a clustering algorithm that groups the plurality of users into clusters based on the user data for the plurality of users;

obtaining, by the one or more computing devices, menstrual cycle data for a user;

obtaining, by the one or more computing devices, biometric data collected from the user using one or more sensors;

determining, by the computing device based on the biometric data and the menstrual cycle data, a first value for a biometric indicator during a first menstrual cycle phase and a second value for the biometric indicator during a second menstrual cycle phase;

determining, by the computing device, a difference between the first value for the biometric indicator during the first menstrual cycle phase to the second value for the biometric indicator during the second menstrual cycle phase;

determining, by the computing device and based on the difference between the first value for the biometric indicator during the first menstrual cycle phase to the second value for the biometric indicator during the second menstrual cycle phase, a menstrual cycle group for the user from the plurality of menstrual cycle groups; and providing, by the one or more computing devices, data representing the determined menstrual cycle group for the user for display to the user.

* * * * *